US009809797B2

(12) United States Patent
Yee et al.

(10) Patent No.: US 9,809,797 B2
(45) Date of Patent: Nov. 7, 2017

(54) ENHANCED GENERATION OF CYTOTOXIC T-LYMPHOCYTES BY IL-21 MEDIATED FOXP3 SUPPRESSION (75) Inventors: Cassian Yee, Seattle, WA (US); Yongqing Li, Shoreline, WA (US)

(73) Assignee: NATIONAL INSTITUTES OF HEALTH (NIH) U.S. DEPT. OF HEALTH AND HUMAN SERVICES (DHHS) DIVISION OF EXTRAMURAL INVENTIONS AND TECHNOLOGY, Washington, DC (US)

( * ) Notice: Subject to any disclaimer, the term of this patent is extended or adjusted under 35 U.S.C. 154(b) by 463 days.

(21) Appl. No.: 12/677,035

(22) PCT Filed: Sep. 25, 2008

(86) PCT No.: PCT/US2008/011088
§ 371 (c)(1),
(2), (4) Date: Apr. 8, 2010

(87) PCT Pub. No.: WO2009/045308
PCT Pub. Date: Apr. 9, 2009

(65) Prior Publication Data
US 2010/0330056 A1  Dec. 30, 2010

Related U.S. Application Data (60) Provisional application No. 60/977,150, filed on Oct. 3, 2007.

(51) Int. Cl.
C12N 5/0783 (2010.01)
A61K 31/41 (2006.01)
A61K 39/00 (2006.01)
A61K 35/17 (2015.01)
A61K 35/12 (2015.01)

(52) U.S. Cl.
CPC ........... *C12N 5/0638* (2013.01); *A61K 31/41* (2013.01); *A61K 35/17* (2013.01); *A61K 39/00* (2013.01); *C12N 5/0636* (2013.01); *A61K 35/12* (2013.01); *A61K 2035/124* (2013.01); *A61K 2039/51* (2013.01); *A61K 2039/5154* (2013.01); *C12N 2501/23* (2013.01); *C12N 2501/2321* (2013.01); *C12N 2501/998* (2013.01)

(58) Field of Classification Search
None
See application file for complete search history.

(56) References Cited

U.S. PATENT DOCUMENTS

| 5,827,642 A * | 10/1998 | Riddell | C12N 5/0636 424/93.71 |
| 6,316,257 B1 * | 11/2001 | Flyer | C07K 16/2896 435/325 |
| 2001/0031253 A1 * | 10/2001 | Gruenberg | A61K 39/0008 424/93.1 |
| 2006/0121005 A1 * | 6/2006 | Berenson | C12N 5/0636 424/93.7 |

FOREIGN PATENT DOCUMENTS

EP 1795599 A1 6/2007
WO WO 2006065495 A2 * 6/2006

OTHER PUBLICATIONS

Feuerer et al., Nat Immunol. Jul. 2009;10(7):689-95.*
Zhao et al., Exp Biol Med (Maywood) 2013 238: 400.*
Peng et al. (Cancer Immunol Immunother (2012) 61:2183-2192).*
Bisset et al. (Eur J Haematol 2004: 72: 203-212).*
The Memorandum from Deputy Commissioner for Patent Examination Policy Andrew H. Hirshfeld, dated Mar. 4, 2014, 19 pages in total with first page not numbered.*
"Evaluating subject Matter Eligibility Under 35 U.S.C. § 101," Mar. 19, 2014 update, pp. 1-93.*
Onoda et al. (Int I mmunol. Oct. 2007;19(10):1191-9).*
Powell et al. (J Immunother 2005;28:403-411).*
Boettler et al. (J Virol. Jun. 2005;79(12):7860-7).*
Kaka et al. (Blood, (Nov. 16 2006) vol. 108, No. 11, Part 1, pp. 1059A-1060A.)*
Hinrichs et al. (Blood. 2008;111: 5326-5333).*
Cooper et al. (Cytotherapy, 2006, vol. 8, No. 2, 105-117).*
Valmori et al. (Cancer Research 60, 4499-4506, Aug. 15, 2000).*
Straathof et al. (Blood. 2005;105:4247-4254).*
Comes et al. (J Immunol 2006; 176:1750-1758).*
Li Y et al. IL-2 influences the frequency, phenotype, and affinity of the antigen-specific CD8 T cell response. Journal of Immunology. 2005; 175: 2261-2269.
Nair S et al. Vaccination against the forkhead family transcription factor Foxp3 enhances tumor immunity. Cancer Research. 2007; 67(1): 371-380.
Li Y and Yee C. IL-2-mediated Foxp3 suppression leads to enhanced generation of antigen-specific CD8+ cytotoxic T lymphocytes. Blood. Jan. 1, 2008; 111(1): 229-235.
International Search Report and Written Opinion, PCT/US2008/011088, dated Mar. 24, 2009.

* cited by examiner

*Primary Examiner* — Zachary Skelding
(74) *Attorney, Agent, or Firm* — McBee Moore Woodward & Vanik IP, LLC; Susan McBee (57) ABSTRACT A method of carrying out adoptive immunotherapy by administering a subject an antigen-specific cytotoxic T lymphocytes (CTL) preparation in a treatment-effective amount is described. In the method, the CTL preparation is preferably administered as a preparation of an in vitro antigen-stimulated and expanded primate CTL population, the CTL population: (i) depleted of FoxP3+ T lymphocytes prior to antigen stimulation; (ii) antigen-stimulated in vitro in the presence of interleukin-21; or (iii) both depleted of FoxP3+ T lymphocytes prior to antigen stimulation and then antigen-stimulated in vitro in the presence of interleukin-21. Methods of preparing such compositions, and compositions useful for carrying out the adoptive immunotherapy, are also described.

7 Claims, 6 Drawing Sheets

ENHANCED GENERATION OF CYTOTOXIC T-LYMPHOCYTES BY IL-21 MEDIATED FOXP3 SUPPRESSION

RELATED APPLICATIONS

This application is a 35 U.S.C. §371 national phase application of PCT Application PCT/US2008/011088, filed Sep. 25, 2008, and published in English on Apr. 9, 2009, as International Publication No. WO 2009/045308, and which claims the benefit under 35 U.S.C. §119(e) of U.S. Provisional Patent Application Ser. No. 60/977,150, filed Oct. 3, 2007, the disclosure of each of which is incorporated herein by reference in its entirety.

GOVERNMENT FUNDING

This invention was made with government support under CA083636 awarded by the National Institutes of Health. The government has certain rights in the invention.

FIELD OF THE INVENTION

The present invention concerns methods and compositions for carrying out adoptive immunotherapy.

BACKGROUND OF THE INVENTION

Adoptive cellular therapy of cancer involves ex vivo generation of autologous antigen specific T cells, followed by in vitro expansion and infusion into patients in the hope that transferred T cells will traffic to and eradicate tumor[1,2]. Recent studies have demonstrated tumor regression and measurable clinical benefit in patients who are otherwise refractory to conventional therapy[3,4]. One major obstacle to adoptive therapy has been the feasibility of isolating tumor-reactive T cells. T cells recognizing tumor-associated antigens, which are often normal self proteins, exist at very low frequency and exhibit predominantly low target avidity[5,6] due to central and peripheral tolerance mechanisms. Moreover, such potentially autoreactive T cells may be suppressed by circulating regulatory cells ($T_{reg}$), that can lead to impaired proliferative response to antigenic stimulation.

Regulatory T cells ($T_{reg}$) have been shown to play a critical role in controlling immunologic tolerance to self-antigens as well as presenting a major barrier to the development of effective anti-tumor immunity in animal models[7-9]. In animal models, tumor antigen specific CD8 cells failed to undergo normal functional maturation in the presence of $T_{reg}$ cells and were rendered incapable of destroying specific tumor targets[10]. Conversely, depletion of regulatory T cells controlled the growth of melanoma in most mice and promoted long-lasting CD8+ T-cell-dependent protective immunity[11], possibly through the recruitment of high-avidity antigen specific CTL[12]. Recent evidence of elevated $T_{reg}$ cells in the peripheral blood of patients with cancer[13-16] and the finding that increased prevalence of tumor-associated $T_{reg}$ in situ as a predictor for reduced survival[17] suggest the importance of regulatory control of the endogenous anti-tumor immune response. The suppressive mechanisms at play in vivo[18], may also limit the capacity to generate antigen-specific T cells in vitro.

Expression of the forkhead transcription factor, Foxp3, has been linked to the regulatory phenotype. Although Foxp3 is a reliable marker of naturally occurring $T_{reg}$, as an intracellular protein, it cannot be used as a practical method of sorting for viable $T_{reg}$ cells. Instead, it has been shown that CD4+ cells constitutively expressing $CD25^{hi}$, are also FoxP3+. We and others have demonstrated that depletion of CD25+ cells in vitro can lead to enhanced generation of CD4+ T cells recognizing tumor-associated self antigens[19] presumably by eliminating the inhibitory influence of CD25+ T regs in the PBMC responder population.

IL-21 belongs to the family of gamma-chain receptor cytokines that includes IL-2, IL-7, and IL-15-cytokines that all deliver their intracellular signal through the shared gamma-chain receptor and influence T cell activation and differentiation[20-22]. Recently, we demonstrated that in vitro exposure to IL-21 (in contrast to other gamma-chain receptor cytokines) can lead to the generation of self antigen-specific CTL in increased numbers and with enhanced avidity and function[23]. In light of work demonstrating that barriers to optimal T cell development may involve a regulatory component, we postulate that IL-21 may influence the regulatory control of cellular responses to tumor self proteins in vitro.

SUMMARY OF THE INVENTION

A first aspect of the present invention is, in a method of carrying out adoptive immunotherapy in a primate subject in need thereof by administering the subject an antigen-specific cytotoxic T lymphocytes (CTL) preparation in a treatment-effective amount, the improvement comprising: administering as the CTL preparation a preparation consisting essentially of an in vitro antigen-stimulated and expanded primate CTL population, the CTL population: (z) depleted of FoxP3+ T lymphocytes (or depleted of CD25+ cells) prior to antigen stimulation; (ii) antigen-stimulated in vitro in the presence of interleukin-21; or (iii) both depleted of FoxP3+ T lymphocytes (or depleted of CD25+ cells) prior to antigen stimulation and then antigen-stimulated in vitro in the presence of interleukin-21.

A second aspect of the present invention is a pharmaceutical formulation comprising or consisting essentially of an in vitro expanded primate cytotoxic T lymphocyte (CTL) population, the CTL population depleted of FoxP3+ T lymphocytes (or depleted of CD25+ cells) prior to antigen stimulation and the CTL population antigen-stimulated in vitro in the presence of interleukin-21.

A further aspect of the present invention is the use of a formulation as described herein for the preparation of a medicament for treating cancer, or for treating an infectious disease, in a primate subject in need thereof.

A further aspect of the invention is a method of making a cytotoxic T lymphocyte (CTL) preparation useful for adoptive immunotherapy; the method comprising the steps of: (a) optionally (but in some embodiments preferably) separating a lymphocyte subpopulation depleted of FoxP3+ cells (or depleted of CD25+ cells) therefrom from a first lymphocyte population collected from a donor; (b) enriching for antigen-specific CTL in the subpopulation in vitro in a culture medium optionally (but in some embodiments preferably) containing interleukin-21; and then (c) collecting cells from the culture medium to produce the CTL preparation.

In some embodiments of the invention, the FoxP3+ cells (or CD25+ cells) are depleted in the CTL preparation at least 2, 5, 10, 50 100-fold, and the number of antigen specific CD8+ CTL are enriched in the CTL preparation at least 5, 10, 50, 100 or 200-fold, as compared to that seen in the same CTL preparation not subjected to the separating step (b) and where interleukin-21 is not included in the culture medium in the expanding step (c).

A further aspect of the invention is an in vitro expanded primate cytotoxic T lymphocyte (CTL) preparation produced by the processes described herein.

A further aspect of the invention is, in a method of carrying out adoptive immunotherapy in a primate subject in need thereof by administering the subject an antigen-specific cytotoxic T lymphocytes (CTL) preparation in a treatment-effective amount, the improvement comprising: administering as the CTL preparation a preparation consisting essentially of an in vitro antigen-stimulated and expanded primate CTL population, the CTL population depleted of FoxP3+ T lymphocytes prior to antigen stimulation in vitro; while concurrently administering the subject interleukin-21 in an amount effective to promote the expansion of the antigen-specific cytotoxic T lymphocytes in the subject. (ii) antigen-stimulated in vitro in the presence of interleukin-21; or (iii) both depleted of FoxP3+ T lymphocytes prior to antigen stimulation and then antigen-stimulated in vitro in the presence of interleukin-21.

A further aspect of the invention is, in a method of carrying out adoptive immunotherapy in a primate subject in need thereof by administering the subject an antigen-specific cytotoxic T lymphocytes (CTL) preparation in a treatment-effective amount, the improvement comprising: administering the subject a CD25 depletion agent (e.g., daclizumab, diphtheria toxin conjugated to IL-2) in an amount effective to deplete the CTL population of FoxP3+ T lymphocytes in the subject; and concurrently administering the subject interleukin-21 in an amount effective to promote the expansion of the antigen-specific cytotoxic T lymphocytes in the subject.

A further aspect of the invention is the use of interleukin-21 for the preparation of a medicament for promoting the expansion of antigen-specific cytotoxic T lymphocytes (CTL) in a subject receiving adoptive immunotherapy by administration of the CTLs.

A further aspect of the invention is the use of a CD25 depletion agent (e.g., denileukin diftitox or a pharmaceutically acceptable salt thereof; e.g., Ontak®) for the preparation of a medicament for depleting a CTL population of FoxP3+ T lymphocytes in a subject receiving adoptive immunotherapy by administration of the CTLs.

The foregoing and other objects and aspects of the present invention are explained in greater detail in the drawings herein and the specification below.

BRIEF DESCRIPTION OF THE DRAWINGS

FIG. 1. Combined use of IL-21 and CD25 depletion leads to significantly enhanced generation of antigen-specific CTL. Unmanipulated or CD25-depleted PBMC from HLA-A2+ patients with melanoma were stimulated in vitro with autologous mature dendritic cells pulsed with the MART-1, M26 peptide as described in 'Materials and Method'. Where indicated, IL-21 (30 ng/ml) was added at culture initiation. A. After two cycles of stimulation $5 \times 10^5$ Cells from each experiment group were harvested and stained with 20 µg/ml of peptide/MHC tetramer (PE, vertical axis) and FITC-conjugated CD4, a vital dye (DAPI) was also added to exclude dead cells. Data are expressed as percentage of tetramer positive cells among gated lymphocytes on day 18 after $2^{nd}$ stimulation. B. The absolute number in millions of tetramer+ cells corresponding to each experimental culture from a representative melanoma patient depicted in A., and the fold increase in absolute numbers of CD25 depletion and/or IL-21 treated to untreated cultures (Control). Representative results from three separate experiments are presented.

FIG. 2. Combined use of Il-21 and CD25 depletion enhances generation of WT-1 and NY-ESO-1-specific CTL responses. Unmanipulated or CD25-depleted PBMC from an HLA-A2+ patient with a WT-1+ ovarian cancer (FIG. 2A, above) and a patient with melanoma (NY-ESO seropositive) were stimulated as described in FIG. 1. The increase in absolute number of WT-1 or NY-ESO-1-specific CTL as well as the fold increase in numbers compared to control cultures are shown in FIG. 2B.

FIG. 3. IL-21 is unique among γ-chain receptor cytokines in its ability to induce expansion of antigen-specific CTL. Unmanipulated or CD25-depleted PBMC from HLA-A2+ patients with melanoma were stimulated in vitro with autologous mature dendritic cells pulsed with the MART-1, M26 peptide as described in 'Materials and Method'. Optimal concentrations of IL-2 (12.5 U/ml), IL-7 (10 ng/ml), IL-15 (30 U/ml), and IL-21 (30 ng/ml) were added to individual cultures at time of stimulation on Day 1. $5 \times 10^5$ cells from each experiment group were harvested on Day 7 and stained with 20 µg/ml of peptide/MHC tetramer-PE and PerCP-conjugated CD8. Data are expressed as percentage of tetramer positive cells among gated lymphocytes.

FIG. 4. IL-21-treated cultures enrich for a population of $CD28^{hi}$ Ag-specific memory CTL. Cells were collected 7 days after $2^{nd}$ stimulation with MART-1 peptide-pulsed autologous DCs and stained for MART-1-tetramer and simultaneously with either CD28, CCR7 and CD45RA under the conditions described: PBMC (untreated control culture), PBMC+IL-21 (addition of IL-21 at 30 ng/ml during the first stimulation), CD25 depl (CD25-depleted PBMC used as a source of T cells) and CD25depl+IL-21 (combined CD25 depletion and IL-21 treatment). These results are representative of cultures from three donors.

FIG. 6. IL-21 partially reverses $T_{reg}$-mediated inhibition of CD8 T cell proliferation. A) Sorted $T_{reg}$ cells ($5 \times 10^4$/well) were cultured with IL-2 (12.5 U/ml), IL-7 (10 ng/ml), IL-15 (30 ng/ml) or IL-21 (30 ng/ml) in the presence or absence of anti-CD3 and autologous dendritic cells; B) Sorted CD8+ CD25– effector T cells ($5 \times 10^4$/well) were cultured with Treg cells at ratio of 1:1 (CD8+:Treg) in the presence of anti-CD3 and autologous dendritic cells. IL-21 (30 ng/ml) was added as indicated.

Proliferation was measured by $^3$H thymidine incorporation pulsed on day 3 and harvested 16~20 hours later. The results of CPM were calculated from triplicate wells with standard error of the mean. The p value was obtained by applying paired sample t test to evaluate the influence of $T_{reg}$ on the CD8 proliferation with and without IL-21.

The present invention is explained in greater detail below. The disclosures of all United States patent references cited herein are incorporated by reference herein in their entirety.

DETAILED DESCRIPTION OF THE PREFERRED EMBODIMENTS

"T cells" or "T lymphocytes" as used herein may be from any mammalian, preferably primate, species, including monkeys, dogs, and humans. In some embodiments the T cells are allogenic (from the same species but different donor) as the recipient subject; in some embodiments the T cells are autologous (the donor and the recipient are the same); in some embodiments the T cells are syngeneic (the donor and the recipients are different but are identical twins).

Cytotoxic T lymphocyte (CTL) as used herein refers to a T lymphocyte that expresses CD8 on the surface thereof (i.e., a $CD8^+$ T cell). CTLs administered to patients or subjects are, in general, "antigen-specific" in that they specifically bind to a tumor-associated antigen and are able to specifically recognize and lyse cells of that tumor, or specifically bind to a microbe-associated antigen and are able to specifically recognize and lyse that microbe.

"Enriched" and "depleted" as used herein to describe amounts of cell types in a mixture refers to the subjecting of the mixture of the cells to a process or step which results in an increase in the number of the "enriched" type and a decrease in the number of the "depleted" cells. Thus, depending upon the source of the original population of cells subjected to the enriching process, a mixture or composition may contain 60, 70, 80, 90, 85, or 99 percent or more (in number or count) of the "enriched" cells and 40, 30, 20, 10, 5 or 1 percent or less (in number or count) of the "depleted" cells.

"Interleukin-21" or "IL-21" (also previously referred to as Zalpha11 Ligand) is known. The term IL-21 as used herein is intended to include natural IL-21 (e.g., mammalian, primate or particularly human IL-21), and recombinant IL-21, as well as active fragments and analogs thereof. Natural and recombinant IL-21 and active fragments and analogs thereof are all known and described in, for example, U.S. Pat. No. 6,686,187 to Novak et al. (ZymoGenetics); U.S. Pat. No. 7,250,274 to Chan et al. (ZymoGenetics); US Patent Application 2007/0178063 to Kindsvogel et al. (ZymoGenetics); US Patent Application 2007/0071717 to Weiner et al. (University of Iowa); US Patent Application 2006/0159655 to Collins et al. (Wyeth); and US Patent Application 2005/0124044 to Cunningham et al. (Johnson & Johnson).

"Treat" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Concurrently" means sufficiently close in time to produce a combined effect (that is, concurrently may be simultaneously, or it may be two or more events occurring within a short time period before or after each other).

I. Antigen Stimulation and In Vitro Expansion.

Antigen stimulation is the process of enriching for a population of antigen-specific T cells by stimulating with antigen or antigen fragment (peptide) in vitro and expansion is the method use to expand (in the case of REM—non-specifically, but it can also be expanded specifically using antigen or antigen fragments), the T cells used for adoptive therapy. Expansion typically utilizes allogeneic irradiated feeder cells; Antigen stimulation typically does not; however antigen-stimulation does require the antigen or antigen fragment to be presented by autologous simulator cells.

In this invention a lymphokine, particularly IL-21, is used during antigen stimulation. Optionally, a lymphokine such as IL-21 may also be used during expansion to suppress the outgrowth of FoxP3+/Treg cells during the expansion process.

T lymphocytes can be collected from a suitable donor in accordance with known techniques and stimulated, enriched or depleted by known techniques such as affinity binding to antibodies such as flow cytometry and/or affinity binding. After enrichment and/or depletion steps, in vitro expansion of the desired T lymphocytes can be carried out in accordance with known techniques (including but not limited to those described in U.S. Pat. No. 6,040,177 to Riddell et al.), or variations thereof that will be apparent to those skilled in the art.

Depletion of FoxP3+ cells can be carried out by any suitable means, such as by depletion of $CD25^+$ cell, or any other physical means of removing FoxP3+ in vitro, such as depletion of cells bearing other Treg surface markers, including but not limited to GITR, positive selection with CD127-pos cells for stimulation (Tregs are often CD127-neg) More particularly, depletion of $CD25^+$ cells from an initial population may be carried out by any suitable technique, such as by contacting the cells to a solid support (e.g. beads) having anti-CD25 antibodies immobilized thereon, so that cells expressing CD25 are bound to the solid support, and then separating the remaining cell subpopulation from the solid support.

The cells are preferably expanded in vitro following the in vitro antigen-stimulation (or enrichment) step. Expansion in vitro may be carried out by any suitable technique. For example, the desired T cell population or subpopulation may be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). The order of additional of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least about 25 degrees Celsius, preferably at least about 30 degrees, more preferably about 37 degrees.

Interleukin-21 may be included in or added to the culture medium in any suitable amount, typically at least 1, 2 or 5 nanograms per milliliter, up to 200, 500 or 1000 nanograms per milliliter, or more. The amount can be adjusted and optimized for particular types of interleukin-21 and particular culture techniques by simply monitoring the amount of $FoxP3^+$ cells in the expanded product, and/or monitoring the amount of antigen-specific CTLs in the expanded product, and adjusting the amount as indicated or desired.

The T lymphocytes expanded are typically cytotoxic T lymphocytes (CTL) that are specific for an antigen present on a human tumor or a pathogen.

The non-dividing feeder cells can comprise gamma-irradiated PBMC feeder cells. In some embodiments, the PBMC are irradiated with gamma rays in the range of about 3000 to 3600 rads.

Optionally, the expansion method may further comprise the step of adding non-dividing EBV-transformed lymphoblastoid cells (LCL) as feeder cells. LCL can be irradiated with gamma rays in the range of about 6000 to 10,000 rads. The LCL feeder cells may be provided in any suitable amount, such as a ratio of LCL feeder cells to initial T lymphocytes of at least about 10:1.

Optionally, the expansion method may further comprise the step of adding anti-CD3 monoclonal antibody to the culture medium (e.g., at a concentration of at least about 0.5 ng/ml). Optionally, the expansion method may further comprise the step of adding IL-2 and/or IL-15 to the culture medium (e.g., wherein the concentration of IL-2 is at least about 10 units/ml).

In some embodiments it may be desired to introduce functional genes into the T cells to be used in immunotherapy in accordance with the present invention. For example, the introduced gene or genes may improve the efficacy of therapy by promoting the viability and/or function of transferred T cells; or they may provide a genetic marker to permit selection and/or evaluation of in vivo survival or migration; or they may incorporate functions that improve the safety of immunotherapy, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al., describing the use of bifunctional selectable fusion genes derived from fusing a dominant positive selectable marker with a negative selectable marker. This can be carried out in accordance with known techniques (see, e.g., U.S. Pat. No. 6,040,177 to Riddell et al. at columns 14-17) or variations thereof that will be apparent to those skilled in the art based upon the present disclosure.

Various infection techniques have been developed which utilize recombinant infectious virus particles for gene delivery. This represents a currently preferred approach to the transduction of T lymphocytes of the present invention. The viral vectors which have been used in this way include virus vectors derived from simian virus 40, adenoviruses, adeno-associated virus (AAV), and retroviruses. Thus, gene transfer and expression methods are numerous but essentially function to introduce and express genetic material in mammalian cells. Several of the above techniques have been used to transduce hematopoietic or lymphoid cells, including calcium phosphate transfection, protoplast fusion, electroporation, and infection with recombinant adenovirus, adeno-associated virus and retrovirus vectors. Primary T lymphocytes have been successfully transduced by electroporation and by retroviral infection.

Retroviral vectors provide a highly efficient method for gene transfer into eukaryotic cells. Moreover, retroviral integration takes place in a controlled fashion and results in the stable integration of one or a few copies of the new genetic information per cell.

It is contemplated that overexpression of a stimulatory factor (for example, a lymphokine or a cytokine) may be toxic to the treated individual. Therefore, it is within the scope of the invention to include gene segments that cause the T cells of the invention to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., Cell 11:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments it may be useful to include in the T cells a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the aminoglycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

Preferably, the positive selectable marker and the negative selectable element are linked such that loss of the negative selectable element necessarily also is accompanied by loss of the positive selectable marker. Even more preferably, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al, Mol. and Cell. Biology 11:3374-3378, 1991. In addition, in preferred embodiments, the polynucleotides of the invention encoding the chimeric receptors are in retroviral vectors containing the fused gene, particularly those that confer hygromycin B resistance for positive selection in vitro, and ganciclovir sensitivity for negative selection in vivo, for example the HyTK retroviral vector described in Lupton, S. D. et al. (1991), supra. See also the publications of PCT/US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene.

A variety of methods can be employed for transducing T lymphocytes, as is well known in the art. For example, retroviral transductions can be carried out as follows: on day 1 after stimulation using REM as described herein, provide the cells with 20-30 units/ml IL-2; on day 3, replace one half of the medium with retroviral supernatant prepared according to standard methods and then supplement the cultures with 5 ug/ml polybrene and 20-30 units/ml IL-2; on day 4, wash the cells and place them in fresh culture medium supplemented with 20-30 units/ml IL-2; on day 5, repeat the exposure to retrovirus; on day 6, place the cells in selective medium (containing, e.g., an antibiotic corresponding to an antibiotic resistance gene provided in the retroviral vector) supplemented with 30 units/ml IL-2; on day 13, separate viable cells from dead cells using Ficoll Hypaque density gradient separation and then subclone the viable cells.

II. Compositions and Methods.

Subjects that can be treated by the present invention are, in general, human and other primate subjects, such as monkeys and apes for veterinary medicine purposes. The subjects can be male or female and can be any suitable age, including infant, juvenile, adolescent, adult, and geriatric subjects.

Subjects that can be treated include subjects afflicted with cancer, including but not limited to colon, lung, liver, breast, prostate, ovarian, skin (including melanoma), bone, and brain cancer, etc. In some embodiments the tumor associated antigens are known, such as melanoma, breast cancer, squamous cell carcinoma, colon cancer, leukemia, myeloma, prostate cancer, etc. (in these embodiments memory T cells can be isolated or engineered by introducing the T cell receptor genes). In other embodiments the tumor associated proteins can be targeted with genetically modified T cells expressing an engineered immunoreceptor. Examples include but are not limited to B cell lymphoma, breast cancer, prostate cancer, and leukemia.

Subjects that can be treated also include subjects afflicted with, or at risk of developing, an infectious disease, including but not limited to viral, retroviral, bacterial, and protozoal infections, etc.

Subjects that can be treated include immunodeficient patients afflicted with a viral infection, including but not limited to Cytomegalovirus (CMV), Epstein-Barr virus (EBV), adenovirus, BK polyomavirus infections in transplant patients, etc.

Cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumen.

A treatment-effective amount of cells in the composition is at least $10^9$, typically greater than $10^9$, at least $10^{10}$ cells, and generally more than $10^{10}$. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 mls or less, even 250 mls or 100 mls or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^9$, $10^{10}$ or $10^{11}$ cells.

In some embodiments, the lymphocytes of the invention may be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, the cells are usually administered by infusion, with each infusion in a range of at least $10^6$ to $10^{10}$ cells/m$^2$, preferably in the range of at least $10^7$ to $10^9$ cells/m$^2$. The clones may be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein. See, e.g., U.S. Pat. No. 6,040,177 to Riddell et al. at column 17.

III. Active Agents for In Vivo Administration.

In some embodiments of the invention, subjects being treated are administered a CD25+ cell depleting agent. Depletion of such cells can be effected using any of a variety pharmaceutically acceptable agents, including small molecules and antibodies (e.g., monoclonal antibodies, preferably, humanized monoclonal antibodies). Antibodies that bind specifically to the alpha subunit (p55 alpha, CD25, or Tac subunit) of the human high-affinity interleukin-2 receptor that is expressed on the surface of activated lymphocytes are particularly preferred, ZENAPAX (daclizumab) being a specific example. Alternatively, diphtheria toxin conjugated to IL-2, such as ONTAK, can be used (e.g., in humans) to effect transient depletion of T regulatory cells. See, e.g., B Haynes et al., US Patent Application Publication No. 2006/0165687 at paragraph 39 therein. Such compounds are sometimes referred to as "active agents" or "active compounds" herein.

In some embodiments of the invention, subjects being treated are administered IL-21 as an active agent. Such agents (also sometimes referred to as "active agents" or "active compounds" herein) are known as described above.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

The active compounds described above may be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Dosages of active agents may be determined in accordance with known techniques. For example, the dosage of a diptheria toxin-interleukin-2 fusion such as ONTAK may be from 1, 2 or 5 mcg/kg/day up to about 20, 40 or 50 mcg/kg/day, typically administered intravenously (e.g., for one, two, three, four or five consecutive days or more), with each administration preferably delivered as an infusion over time (e.g., from 10 to 20 minutes) rather than as a bolus injection. In an additional example, the dosage of an antibody such as ZENAPAX may be be from 0.1, or 0.5 mg/kg up to 2, 5 or 10 mg/kg. Dosage will of course vary depending upon the particular active agent and formulation, as well as the age and condition of the subject, as is known in the art.

The present invention is illustrated further in the examples set forth below.

Experimental

A. Materials and Methods.

Depletion of CD25+ $T_{reg}$ Cells.

Depletion of CD25+ T cells was performed using the CliniMACS CD25 MicroBeads (Miltenyi Biotech) according to manufacture's instruction. In brief, the leukapheresis product was washed and resuspended in PBS/EDTA (2 mM, invitrogen) supplemented with 0.5% human serum albumin (Life Technologies, Gaithersburg, Md.). Appropriate amount of CD25 MicroBeads was added and incubated for 15 minutes at room temperature with gentle mixing every five minutes. Cells were washed, resuspended, and applied to the AutoMACS instrument with the CD25 depletion program selected. Upon completion of the depletion, an aliquot of cell fraction was stained for CD25 following FACScan analysis to check the efficiency of CD25 MicroBeads depletion.

Antibody Plus Peptide-MHC Tetramer Staining of T Cells.

APC labeled M26-MHC-Tetramer was produced in the immune monitoring lab at Fred Hutchinson Cancer Center based on previously described protocols[24]. For sample analysis, $0.5 \times 10^6$ cells in 25 µl of 2% FCS/PBS were first stained with peptide tetramer—APC (final concentration of 20 µg MHC/ml) for one hour at room temperature, followed by anti-CD8-FITC or PerCP (BD, PharMingen, San Diego, Calif.) staining for 20 min at 4° C. to analyze antigen specific T cell population. In some experiments, measure for phenotypes was carried out by anti-CD28-APC (BD, PharMingen, San Diego, Calif.) or anti-CD28-FITC (Caltag Lab, Burlingame, Calif.), anti-CCR7-PE and anti-CD45RO or anti-CD45RA-FITC (BD, PharMingen, San Diego, Calif.) staining. After washing with PBS, cells were resuspended in PBS containing 2% FBS and DAPI was added. Data were acquired using a FACScalibur flow cytometer and CellQuest (BD) and analyzed using FlowJo software (Tree Star, San Carlos, Calif.).

In Vitro Generation of Human Antigen-Specific CD8+ T Cells.

Donor blood was typed by the HLA Typing Lab at the Puget Sound Blood Center (Seattle, Wash.). HLA-A2+ donors were used in the study. MART-1 M26-, NY-ESO-1 NY157- and WT-1 WT126-peptide specific T cells were generated in a manner similar to that previously described[3,23]. DC were generated by exposing adherent PBMC to IL-4 (500 U/ml, R&D) and GM-CSF (800 U/ml, Amgen) in AIM-V medium (Life Technologies) followed by maturation using IL-1β at 2 ng/ml, IL-6 at 1000 U/ml, TNF-α at 10 ng/ml (R&D Systems, Minneapolis, Minn.) and PGE-2 at 1 µg/ml (Sigma) for an additional 2 days. The mature DC population contained more than 90% CD83+ DCs on day 8 as determined by FACS analysis.

Mature DCs were harvested and pulsed with 40 µg/ml of synthesized peptides at $2 \times 10^6$ cell/ml in the presence of 3 µg/ml of β2 microglobulin (Scripps Lab, San Diego, Calif., USA) in PBS with 1% human serum albumin (Life Technologies, Gaithersburg, Md.) for 4 hrs at room temperature. After washing three times with sterile PBS (Life Technologies), DCs were co-cultivated with responder T cells (unmanipulated or CD25-depleted) at $5 \times 10^5$ cells/well in 6 well plate in CTL medium, consisting of RPMI 1640 (Gibco, Carlsbad, Calif.), 25 mM HEPES, 4 mM L-glutamine, 50 µM 2-mercaptoethanol (Gibco), penicillin (50 U/ml), streptomycin (50 mg/ml) (Life Technologies, Gaithersburg, Md.), and 10% pooled human serum from normal donors. Cytokine, IL-21 (30 ng/ml) was added to the experimental wells required after the culture initiated. In some experiments, IL-2 (10 U/ml), IL-7 (10 ng/ml), or IL-15 (10 ng/ml) were added to compare the effect of IL-21. These concentrations of IL-2, IL-7, IL-15 and IL-21 were previously demonstrated to represent optimal dosing; higher concentrations led to no benefit or a detrimental effect in the generation of antigen-specific CTL[23] (and data not shown). For the second stimulation, irradiated autologous PBMCs pulsed with antigenic peptide were used. A total of 5 donors were evaluated, three of them for MART-1 specific responses and two others patients (ovarian cancer and NY-ESO seropositive melanoma donor) for WT-1 and NY-ESO-1 responses, respectively). Unless otherwise specified, results were obtained at 7 days after the $2^{nd}$ in vitro stimulation.

Antibody Plus Peptide-MHC Tetramer Staining of T Cells.

APC labeled peptide-MHC-Tetramers were produced in the Immune Monitoring Lab at Fred Hutchinson Cancer Center using established protocols[24]. For sample analysis, $0.5 \times 10^6$ cells in were first stained with peptide tetramer—APC (20 µg MHC/ml) for one hour at room temperature, followed by anti-CD8-FITC or PerCP (BD, PharMingen, San Diego, Calif.) staining for 20 min at 4° C. After PBS wash, cells were resuspended and DAPI added immediately prior to flow cytometric analysis (FACScalibur flow cytometer and CellQuest (BD)) and analyzed using FlowJo software (Tree Star, San Carlos, Calif.).

Intracellular Detection of Foxp3 Protein by FACS Analysis.

Intracellular staining for Foxp3 protein used PE-conjugated anti-human Foxp3 staining set (clone PCH101, eBioscience) according to the manufacturer's instructions. Briefly, $10^6$ cells were stained with FITC-conjugated anti-CD4 antibody (BD Pharmingen) first for 20 min on ice, washed, then re-suspended in Fixation/Permeabilization buffer and incubated for 60 min at 4° C.

Immune Suppression Assay In Vitro.

Suppression assay was carried out based on the published protocol[25] with minor modifications. CD4+CD25− and CD8+CD25− T cells were ($5 \times 10^4$ cells/well) were co-cultured with $T_{reg}$ cells (2.5 or $5 \times 10^4$ cells/well) with 100 ng/mL anti-CD3 antibody (OKT3) in the presence of irradiated (3500 Rad) autologous dendritic cells ($0.5 \sim 1 \times 10^4$ cells/well) in a 96-well flat-bottom plate. Proliferation was assessed by [$^3$H]thymidine (1 µCi [0.037 MBq] per well) incorporation.

B. Results.

The Combination of CD25 Depletion and IL-21 Markedly Augments the Expansion of Antigen-Specific CD8+ T Cells Following In Vitro Stimulation.

MART-1 specific CTL was generated according to methods described above under the following conditions: no manipulation (Control cultures), IL-21 treatment alone, CD25 depletion alone and IL-21 treatment with CD25-depleted responder PBMCs. IL-21 was used at a dose of 30 ng/ml, previously shown to be optimal for generating antigen specific T cells[26]. Concentrations of 10 ng/ml or less had no effect and inhibition was observed when IL-21 concentration was used at 100 ng/ml or greater.

Figure 1:
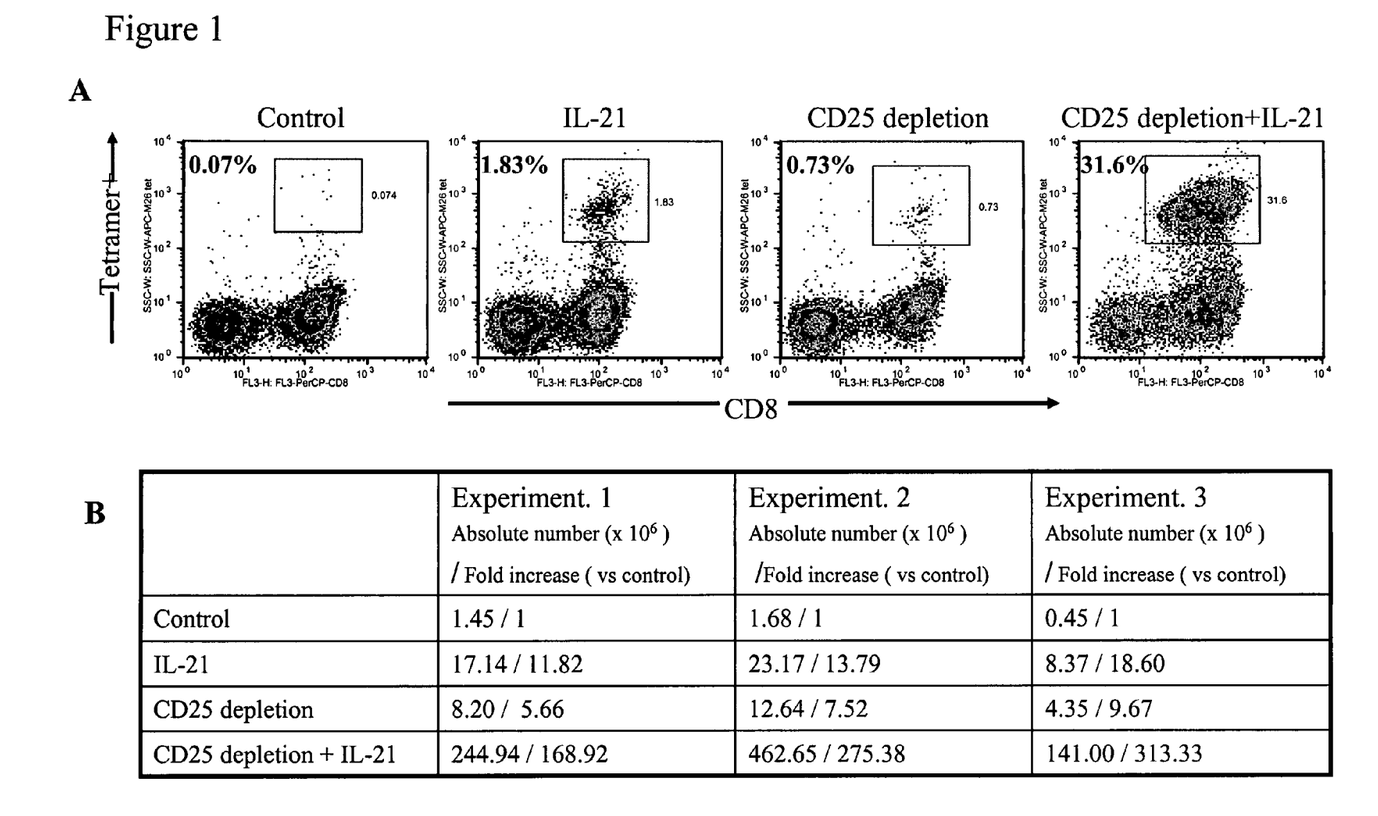

Exposure to IL-21 added once during the first in vitro stimulation led to a marked enhancement in the frequency of MART-1 specific CTL that could be generated (FIG. 1A: 1.83 vs. 0.07%), confirming our previous findings. CD25 depletion alone led to a 10-fold increase in the frequency of antigen specific CD8+ T cells compared with control cultures (0.73 vs. 0.07%). A striking >450-fold increase in the frequency of antigen specific CD8+ T cells was observed through the combined use of CD25 depletion and IL-21 treatment (31.6 vs. 0.07%). Data from three additional patients demonstrated a 160 to >300-fold increase in the absolute numbers of antigen-specific CTL that could be generated with combined CD25 depletion and IL-21 treatment (FIG. 1B: 1.45 vs. 244.94, 1.68 vs. 462.65, 0.45 vs. 141.0). Antigen specific T cells generated by CD25 depletion plus IL-21 demonstrated robust killing activity against antigen-expressing tumor target (>50% lysis at an E:T of 10:1) and IFN-gamma secretion upon recognition of specific peptide antigen in vitro assay (Data not shown).

Figure 2:
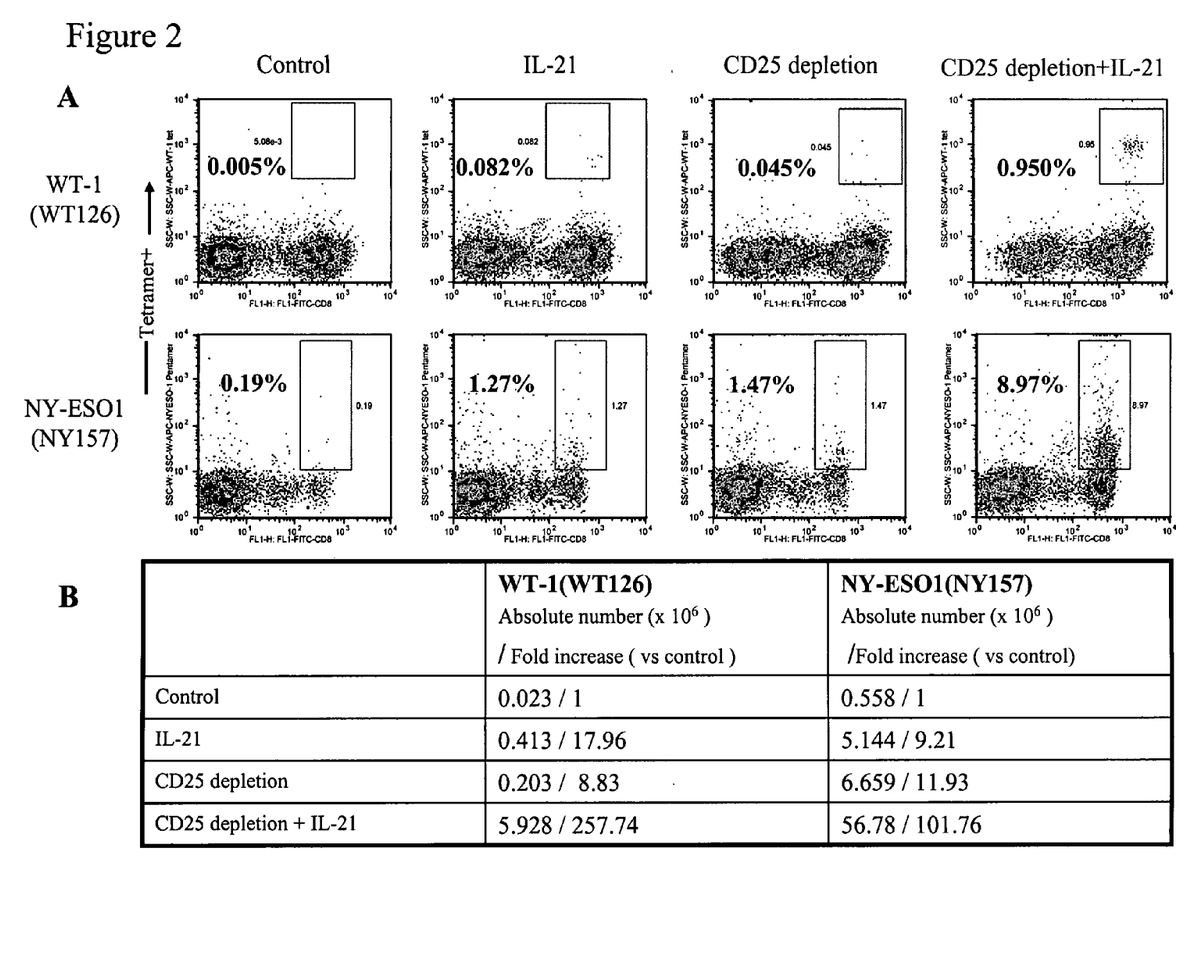

For these initial studies, we used a canonical tumor antigenic epitope—M26 peptide of the melanoma-associated self antigen, MART-1. To evaluate the generality of this finding, we examined CTL responses to two other tumor-associated antigens, WT-1 and NY-ESO-1 in HLA-A*0201+ patient donors. Representative results are shown for responses generated from the PBMC of a patient donor with WT-1+ ovarian tumor and the PBMC of an NY-ESO-1 seropositive patient donor with melanoma (FIG. 2) Although the endogenous precursor frequency of CTL specific for WT-1 (a self antigen that is prevalent at low levels among normal tissues) is very low and the ability to enrich for this rare population of WT-1-specific CTL somewhat elusive (0.005% after two in vitro stimulations), the positive influence of CD25 depletion and IL-21 exposure are similar to that seen for MART-1-specific CTL responses. A 8-20 fold increase in the numbers and frequency of WT-1-specific CTL is observed with either IL-21 treatment or CD25 depletion alone compared to control, but more than 250-fold greater when cultures receive both CD25 depletion and IL-21 treatment. Similarly, for NY-ESO-1 specific responses, a relative 10-fold increase with either treatment alone, increases to 100-fold with combined CD25 depletion and IL-21 exposure.

IL-21 Exposure Leads to Optimal Expansion of Antigen-Specific CTL Following CD25 Depletion.

Figure 3:
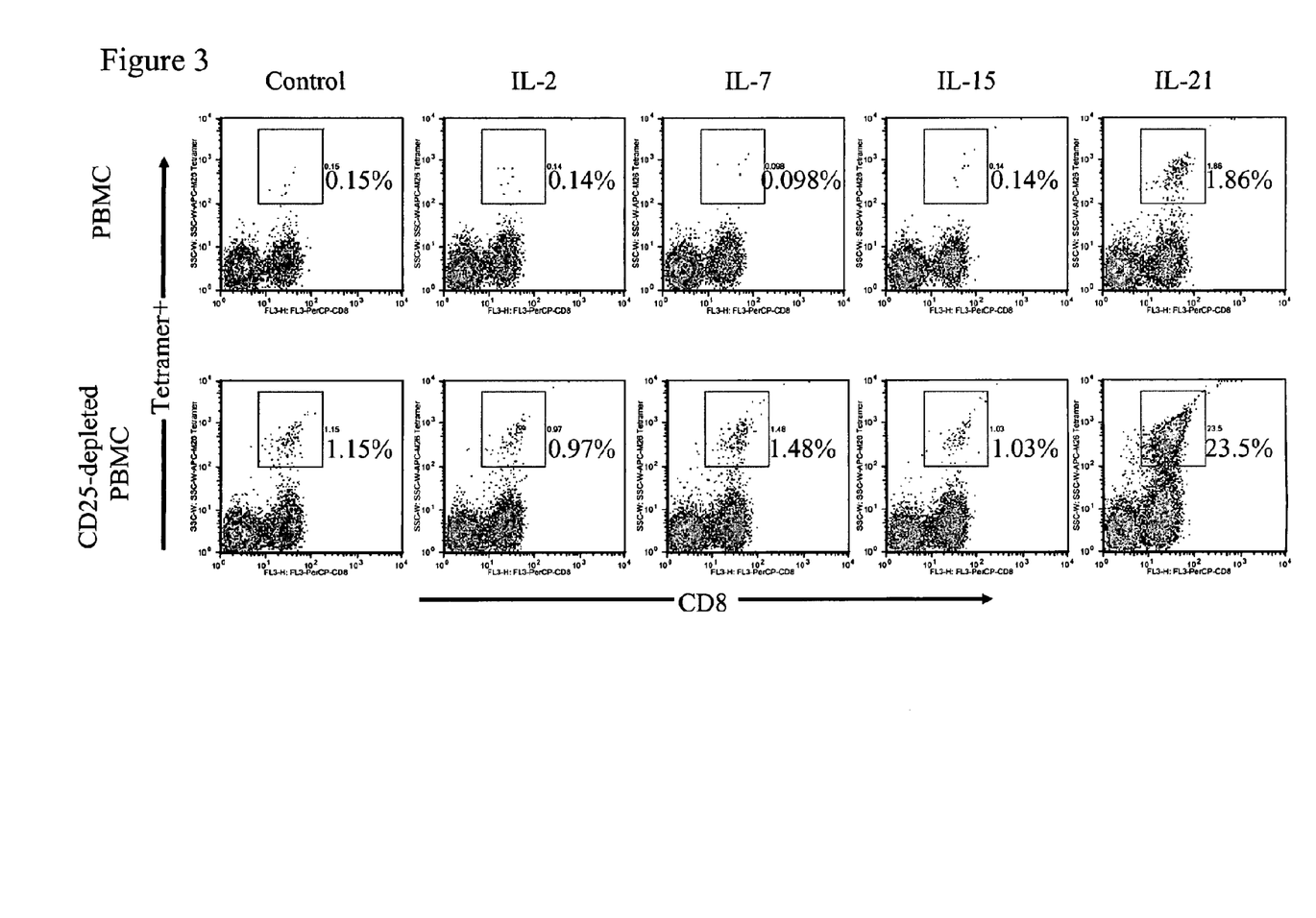

Among the γ-chain receptor cytokines, including IL-2, IL-7 and IL-15, IL-21 provided the greatest effect on antigen-specific CTL expansion following CD25 depletion (FIG. 3). When using untreated PBMC, IL-21 elicited a 10-fold or greater increase in antigen-specific CTL compared with no cytokine or IL-2, IL-7 or IL-15-treated cultures in congruence with our previous results.[23] When using CD25-depleted PBMC, IL-21-exposed cultures yielded a 20-fold greater increase in antigen-specific CTL frequency compared to other CD25-depleted cultures.

IL-21 Exposure Enriches for a Population of CD28+ CCR7− CD8+ Memory CTL.

Figure 4:
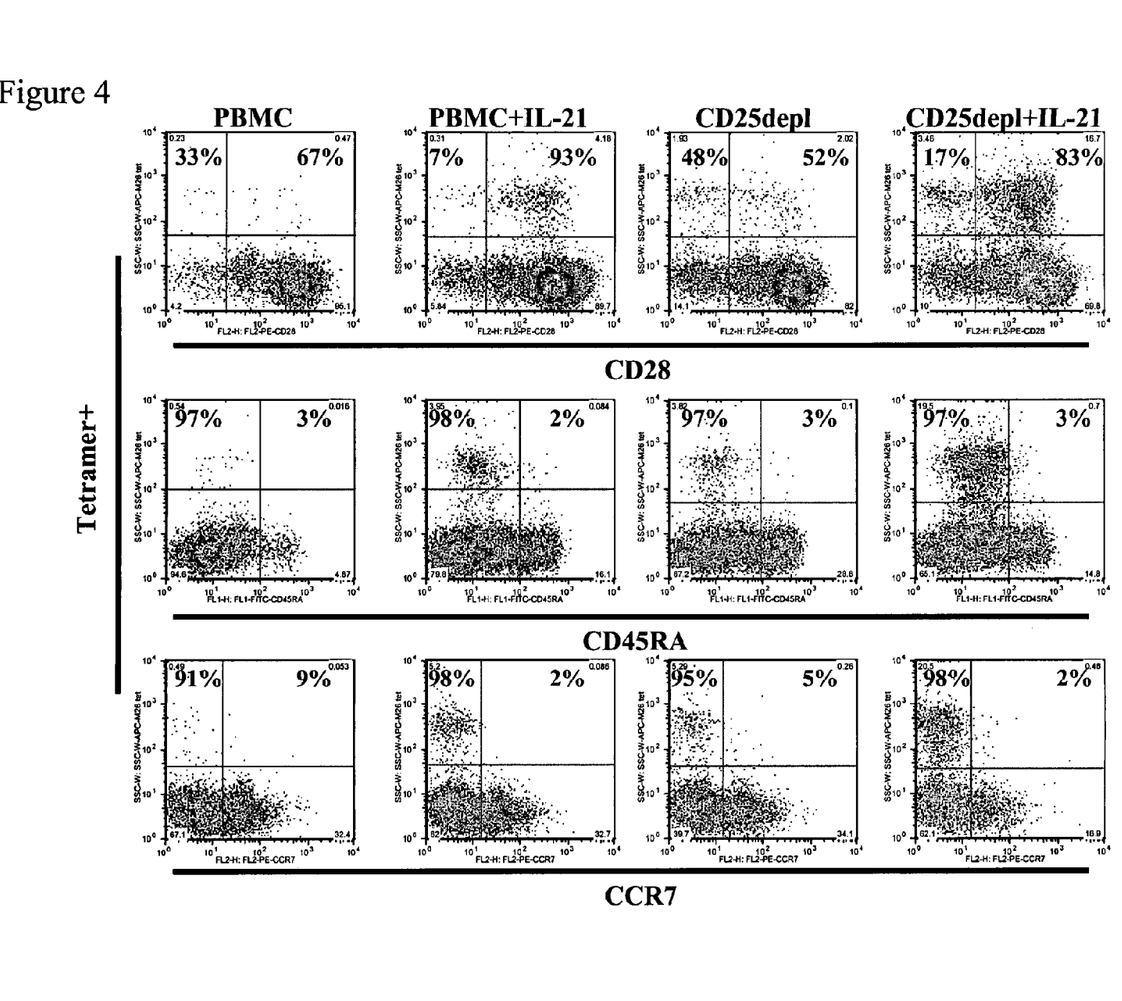

The surface phenotype of antigen-specific CTL generated in cultures under the four conditions (control, IL-21 treatment, CD25 depletion, and combined IL-21 treatment and CD25 depletion) was evaluated by staining for CD28, CCR7, CD45RA expression (FIG. 4). A unique memory phenotype, CD28+, CCR7−, was observed only among the IL-21 exposed cultures (PBMC+IL-21 and CD25depl+IL-2). Results were obtained 7 days after the $2^{nd}$ in vitro stimulation. This phenotype was stable for more than 4 weeks when maintained with IL-2 and IL-7 and without further exposure to IL-21. These findings are consistent with previous studies we have published demonstrating upregulation of CD28 expression and helper-independence among antigen-specific CTL generated in IL-21 treated cultures.[23]

Exposure of CTL Culture to IL-21 Leads to a Decrease in the Frequency of Foxp3+ T Cells.

Figure 5:
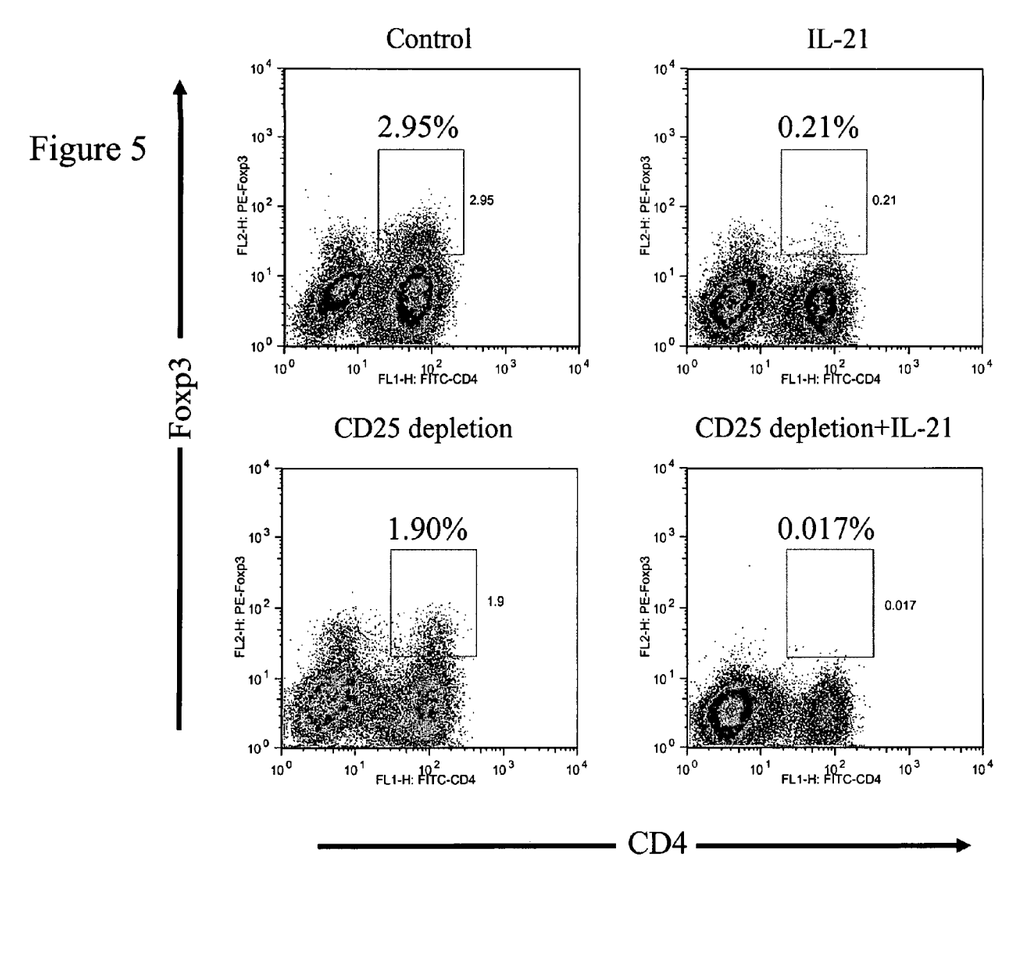
FIG. 5. The frequency of CD4+Foxp3+ T cells is significantly decreased by IL-21 and CD25 treatment in stimulation culture. MART-1-specific T cell stimulation cultures were established using unmanipulated PBMC (control), IL-21-treated, CD25-depleted and CD25 depleted/IL-21-treated PBMC. Three weeks following initial in vitro stimulation, $5 \times 10^5$ cells from each experimental culture were stained with FITC-conjugated CD4, followed by intracellular staining for Foxp3 protein. Data are expressed as percentage of CD4+Foxp3 positive cells among gated lymphocytes.

FoxP3+ cells were identified by intracellular staining following CD25 depletion and/or IL-21 treatment (FIG. 5). CD25 depletion alone led to a measurable decrease in the fraction of FoxP3+ cells in culture. IL-21 treatment alone led to a 10-fold decrease in the fraction of FoxP3+ cells (2.95 to 0.21%). The combination of CD25 depletion and IL-21 treatment resulted in a drop in the CD4+ FoxP3+ population to an almost undetectable level (2.95 to 0.017%); further, a substantial decrease in the fraction of CD4-negative FoxP3+ cells was observed which was not seen with either IL-21 treatment or CD25 depletion alone.

IL-21 Fails to Induce $T_{reg}$ Proliferation.

Figure 6:
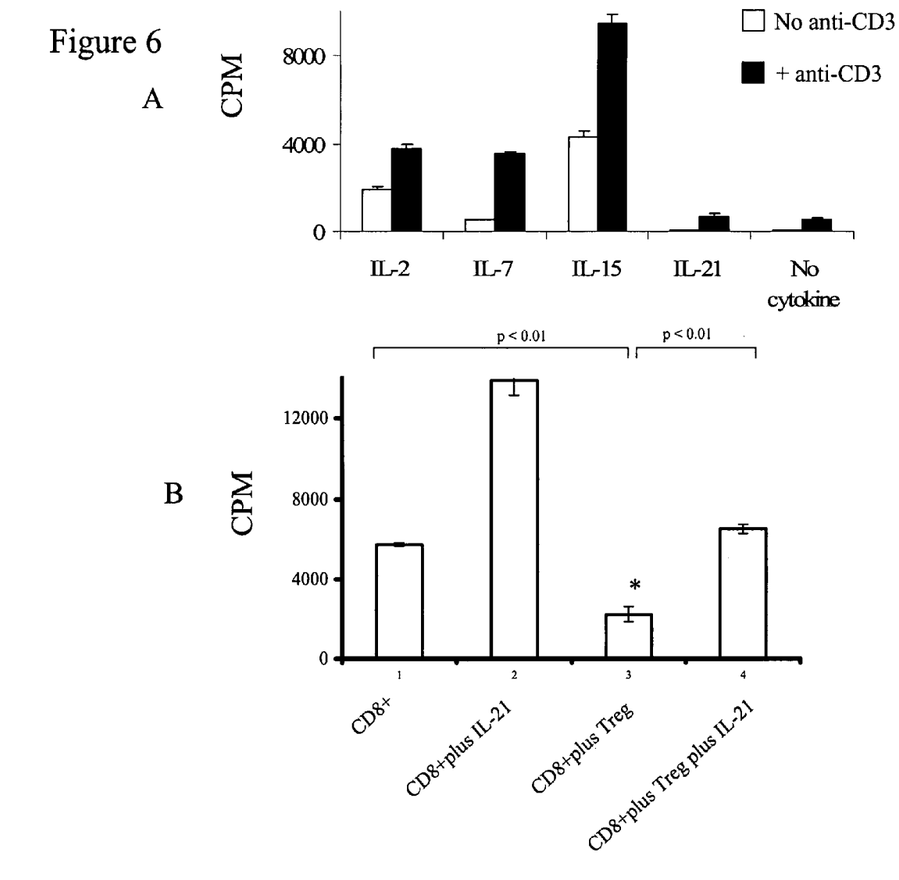

To evaluate the possibility that the differential effects of IL-21, compared with the other gamma-chain receptor cytokines, IL-2, IL-7 and IL-15, was associated with cytokine-mediated $T_{reg}$ proliferation, sorted CD4+ 25+ $T_{reg}$ cells were treated with IL-2, IL-7, IL-15 or IL-21 in the presence or absence of CD3-stimulation (FIG. 6A). Anti-CD3 stimulation led to enhanced $T_{reg}$ proliferation (thymidine uptake) among IL-2, IL-7 and IL-15. IL-15 enhanced $T_{reg}$ expansion in a antigen-independent manner. IL-21 however failed to significantly induce $T_{reg}$ proliferation, even after anti-CD3 stimulation and was no different from the no cytokine culture.

IL-21 Partially Reverses $T_{reg}$-Mediated Suppression of CD8 Proliferation.

When added to CD8+ T cell cultures, $T_{reg}$ cells inhibit proliferation by up to 66% when evaluated by thymidine incorporation assays (FIG. 6B, *p<0.01 vs. CD8+ only). When IL-21 was added at optimal concentration, the suppressive effect of $T_{reg}$ on CD8 T cell proliferation was partially reversed. (FIG. 6B, #p<0.01 vs. CD8+ plus IL-21). Thus, IL-21 not only fails to induce $T_{reg}$ proliferation, but also reverses $T_{reg}$ mediated suppression.

C. Discussion.

Using a prototypic human self antigen we demonstrate for the first time that regulatory T cell depletion can lead to substantially enhanced generation of tumor-associated antigen-specific CTL. The combination of CD25 depletion and IL-21 resulted in a >100-fold depletion of FoxP3+ $T_{reg}$ cells and augmented the frequency and absolute number of tumor-antigen specific CD8+ CTL between 150 and 300-fold. This effect is much greater than that expected given the individual contribution of each factor and is unique for IL-21 since the addition of other γ-chain receptor cytokines such as IL-2, IL-7 and IL-15 did not have a similar effect.

Although CD25 T cell depletion was nearly complete after anti-CD25 immunomagnetic depletion, more than 50% of the FoxP3+ population remained, likely due to the presence of FoxP3+ $T_{reg}$ that do not constitutively express CD25. IL-21 treatment had a greater FoxP3 depleting effect (>90% depletion) and was only able to partially reverse $T_{reg}$-mediated suppression of CD8 T cell proliferation. Perhaps it was the unexpectedly potent combination of both CD25 depletion and IL-21 treatment leading to >99.5% depletion of FoxP3+ cells that enabled a uniquely robust antigen-specific T cell response. We also observed a decrease of FoxP3+ cells not only in the conventional CD4 compartment, but also among CD8+ (CD4-negative) T cells which may represent the putative CD8+ regulatory T cell population recently described.[27,28]

The mechanism of action of IL-21 in this model is unclear. Upon activation, both CD4+ 25+ $T_{reg}$ and CD8+ T cells upregulate IL-21 receptor expression but resting $T_{reg}$ express very low levels of IL-21 receptor (data not shown and[29]). Since $T_{reg}$ are not directly activated in this model, the decrease in FoxP3+ cells following IL-21 treatment in vitro may be due to IL-21 engagement of very low density of surface receptors, the indirect action of IL-21 through intermediate cell types, or expansion of effector cells contributing as a cytokine sink for $T_{reg}$ survival.

In recent studies, IL-21 appears to be a key element in the induction of Th17 cells responsible for proinflammatory and autoimmune responses[30-32]. IL-21 deficient T cells failed to differentiate into Th17 cells and was associated with the reciprocal development of Foxp3 Treg cells suggesting a possible role for IL-21 in mediating decreased levels of Foxp3 in our findings by enhancing the development of Th17 cells at the expense of Treg cells. A genetic basis for these results involving the idd3 gene which regulates the function of Treg cells was suggested.[33] These possible mechanisms are currently under investigation in our model.

The observation that IL-21 treatment leads to depletion of FoxP3+ cells contrasts with results recently published describing the absence of any $T_{reg}$ depleting effect of IL-21 and no beneficial effect on CD8 T cell proliferation in the presence of $T_{reg}$[29]. Our studies have shown that the concentration of IL-21 used may produce confounding results. At concentrations greater or equal to 100 ng/ml, there is no significant beneficial in vitro effect and, in fact, an inhibitory effect. Peluso et al were also unable to address the influence of IL-21 on the generation of antigen-specific CTL since antibodies were used to non-specifically trigger the T cell receptor to reproduce an 'inflammatory' state[29]. The use of anti-CD3 to stimulate through the TCR fails to address issues associated with the generation of tumor-associated-, self-antigen specific T cell responses that arise from a naturally occurring low frequency and low avidity T cell subset.

Our recent experience in human samples demonstrated a beneficial effect of IL-21 on the generation of helper-independent antigen-specific CTL[23]. The impact of IL-21 on $T_{reg}$ cells has only recently been proposed and, until now, not previously shown to directly or indirectly deplete human $T_{reg}$ population. Neither the means to eliminate FoxP3+ cells to such a profound degree nor the capacity to enhance the generation of tumor-associated antigen-specific CTL has previously been demonstrated. By removing regulatory constraints limiting antigen-specific expansion, this strategy may not only improve the prospects for generating tumor-reactive T cells for adoptive cellular therapy, but also uncover novel, tumor-associated targets that were previously below the threshold for generating in vitro T cell responses.

REFERENCES

1. Yee C. Adoptive T-cell therapy of cancer. Hematol Oncol Clin North Am. 2006; 20:711-733.
2. Dudley M E, Rosenberg S A. Adoptive-cell-transfer therapy for the treatment of patients with cancer. Nat Rev Cancer. 2003; 3:666-675.
3. Yee C, Thompson J A, Byrd D, et al. Adoptive T cell therapy using antigen-specific CD8+ T cell clones for the treatment of patients with metastatic melanoma: In vivo persistence, migration, and antitumor effect of transferred T cells. Proc Natl Acad Sci USA. 2002; 99:16168-16173.
4. Dudley M E, Wunderlich J R, Robbins P F, et al. Cancer regression and autoimmunity in patients after clonal repopulation with antitumor lymphocytes. Science. 2002; 298:850-854.
5. Theobald M, Biggs J, Hernandez J, Lustgarten J, Labadie C, Sherman L A. Tolerance to p53 by A2.1-restricted cytotoxic T lymphocytes. Journal of Experimental Medicine. 1997; 185:833-841.
6. Houghton A N. Cancer antigens: immune recognition of self and altered self [comment]. Journal of Experimental Medicine. 1994; 180:1-4.
7. Shimizu J, Yamazaki S, Sakaguchi S. Induction of tumor immunity by removing CD25+CD4+ T cells: a common basis between tumor immunity and autoimmunity. J Immunol. 1999; 163:5211-5218.
8. Onizuka S, Tawara I, Shimizu J, Sakaguchi S, Fujita T, Nakayama E. Tumor rejection by in vivo administration of anti-CD25 (interleukin-2 receptor alpha) monoclonal antibody. Cancer Res. 1999; 59:3128-3133.
9. Sakaguchi S. Naturally arising CD4+ regulatory t cells for immunologic self-tolerance and negative control of immune responses. Annu Rev Immunol. 2004; 22:531-562.
10. Chen M L, Pittet M J, Gorelik L, et al. Regulatory T cells suppress tumor-specific CD8 T cell cytotoxicity through TGF-beta signals in vivo. Proc Natl Acad Sci USA. 2005; 102:419-424.
11. Steitz J, Bruck J, Lenz J, Knop J, Tuting T. Depletion of CD25(+) CD4(+) T cells and treatment with tyrosinase-related protein 2-transduced dendritic cells enhance the interferon alpha-induced, CD8(+) T-cell-dependent immune defense of B16 melanoma. Cancer Res. 2001; 61:8643-8646.
12. Ercolini A M, Ladle B H, Manning E A, et al. Recruitment of latent pools of high-avidity CD8(+) T cells to the antitumor immune response. J Exp Med. 2005; 201:1591-1602.
13. Marshall N A, Christie L E, Munro L R, et al. Immunosuppressive regulatory T cells are abundant in the reactive lymphocytes of Hodgkin lymphoma. Blood. 2004; 103:1755-1762.
14. Javia L R, Rosenberg S A. CD4+CD25+ suppressor lymphocytes in the circulation of patients immunized against melanoma antigens. J Immunother. 2003; 26:85-93.
15. Liyanage U K, Moore T T, Joo H G, et al. Prevalence of regulatory T cells is increased in peripheral blood and tumor microenvironment of patients with pancreas or breast adenocarcinoma. J Immunol. 2002; 169:2756-2761.
16. Woo E Y, Yeh H, Chu C S, et al. Cutting edge: Regulatory T cells from lung cancer patients directly inhibit autologous T cell proliferation. Journal of Immunology. 2002; 168:4272-4276.
17. Curiel T J, Coukos G, Zou L, et al. Specific recruitment of regulatory T cells in ovarian carcinoma fosters immune privilege and predicts reduced survival. Nat Med. 2004; 10:942-949.
18. Turk M J, Guevara-Patino J A, Rizzuto G A, Engelhorn M E, Houghton A N. Concomitant tumor immunity to a poorly immunogenic melanoma is prevented by regulatory T cells. J Exp Med. 2004; 200:771-782.
19. Danke N A, Koelle D M, Yee C, Beheray S, Kwok W W. Autoreactive T cells in healthy individuals. J Immunol. 2004; 172:5967-5972.
20. Ozaki K, Spolski R, Feng C G, et al. A critical role for IL-21 in regulating immunoglobulin production. Science. 2002; 298:1630-1634.
21. Asao H, Okuyama C, Kumaki S, et al. Cutting edge: the common gamma-chain is an indispensable subunit of the IL-21 receptor complex. J Immunol. 2001; 167:1-5.
22. Parrish-Novak J, Dillon S R, Nelson A, et al. Interleukin 21 and its receptor are involved in NK cell expansion and regulation of lymphocyte function. Nature. 2000; 408: 57-63.
23. Li Y, Bleakley M, Yee C. IL-21 influences the frequency, phenotype and affinity of the CD8 T cell response. Journal of Immunology. 2005; (in press).
24. Altman J D, Moss P A H, Goulder P J R, et al. Phenotypic analysis of antigen-specific T lymphocytes [published erratum appears in Science 1998 Jun. 19; 280(5371): 1821]. Science. 1996; 274:94-96.

25. Thornton A M, Shevach E M. CD4+CD25+ immunoregulatory T cells suppress polyclonal T cell activation in vitro by inhibiting interleukin 2 production. J Exp Med. 1998; 188:287-296.

26. Li Y, Bleakley M, Yee C. IL-21 Influences the Frequency, Phenotype, and Affinity of the Antigen-Specific CD8 T Cell Response. J Immunol. 2005; 175:2261-2269.

27. Joosten S A, van Meijgaarden K E, Savage N D, et al. Identification of a human CD8+ regulatory T cell subset that mediates suppression through the chemokine CC chemokine ligand 4. Proc Natl Acad Sci USA. 2007; 104:8029-8034.

28. Bisikirska B, Colgan J, Luban J, Bluestone J A, Herold K C. TCR stimulation with modified anti-CD3 mAb expands CD8+ T cell population and induces CD8+CD25+ Tregs. J Clin Invest. 2005; 115:2904-2913.

29. Peluso I, Fantini M C, Fina D, et al. IL-21 counteracts the regulatory T cell-mediated suppression of human CD4+ T lymphocytes. J Immunol. 2007; 178:732-739.

30. Korn T, Bettelli E, Gao W, et al. IL-21 initiates an alternative pathway to induce proinflammatory T(H)17 cells. Nature. 2007; 448:484-487.

31. Bettelli E, Carrier Y, Gao W, et al. Reciprocal developmental pathways for the generation of pathogenic effector TH17 and regulatory T cells. Nature. 2006; 441:235-238.

32. Nurieva R, Yang X O, Martinez G, et al. Essential autocrine regulation by IL-21 in the generation of inflammatory T cells. Nature. 2007; 448:480-483.

33. Yamanouchi J, Rainbow D, Serra P, et al. Interleukin-2 gene variation impairs regulatory T cell function and causes autoimmunity. Nat Genet. 2007; 39:329-337.

The foregoing is illustrative of the present invention, and is not to be construed as limiting thereof. The invention is defined by the following claims, with equivalents of the claims to be included therein.

That which is claimed is:

1. A pharmaceutical formulation comprising a single T cell population type, wherein said T cell population consists of $CD8^+CD25^-$ antigen-specific human cytotoxic T lymphocyte (CTL) cells specific for an antigen, said formulation being prepared by a process comprising:
    (a) sorting a lymphocyte subpopulation depleted of CD25+ cells from a first lymphocyte population of peripheral blood mononuclear cells (PBMC) to produce a $CD8^+CD25^-$ subpopulation;
    (b) promoting the production of antigen-specific CTL cells in said subpopulation by in vitro culturing the sorted $CD8^+CD25^-$ subpopulation with antigen in a medium containing interleukin-21, wherein the number of antigen specific CD8+ CTL are enriched in said $CD8^+CD25^-$ subpopulation by at least 100-fold, as compared to that seen in the same lymphocyte population not subjected to either said separating step (a) or this promoting step (b); and
    (c) formulating antigen-specific CTL cells produced therefrom into a pharmaceutical formulation, and
    wherein said pharmaceutical formulation comprises at least $10^9$ CTL cells.

2. The formulation of claim 1, wherein said interleukin-21 is included in said culture in an amount of from 1 to 1000 nanograms per milliliter.

3. The formulation of claim 1, wherein the CTL cells are specific for a tumor antigen.

4. The formulation of claim 1, wherein (a) the sorting a lymphocyte subpopulation depleted of $CD25^+$ cells from a first lymphocyte population comprises contacting the first lymphocyte population with anti-CD25 antibodies.

5. The formulation of claim 1, wherein (b) the promoting the production of antigen-specific CTL cells in said subpopulation by in vitro culturing comprises culturing of the CTLs with antigen presenting cells.

6. The formulation of claim 1, wherein the antigen presenting cells comprise dendritic cells (DCs).

7. The formulation of claim 1, wherein the antigen-specific CTL cells comprise a transgene.

* * * * *

UNITED STATES PATENT AND TRADEMARK OFFICE
CERTIFICATE OF CORRECTION

PATENT NO. : 9,809,797 B2  
APPLICATION NO. : 12/677035  
DATED : November 7, 2017  
INVENTOR(S) : Cassian Yee and Yongqing Li Page 1 of 1

It is certified that error appears in the above-identified patent and that said Letters Patent is hereby corrected as shown below:

On the Title Page

Left Column, Item (73), after "Assignee:" delete "NATIONAL INSTITUTES OF HEALTH (NIH) U.S. DEPT. OF HEALTH AND HUMAN SERVICES (DHHS) DIVISION OF EXTRAMURAL INVENTORS AND TECHNOLOGY, Washington DC (US)", and insert: --THE FRED HUTCHINSON CANCER RESEARCH CENTER, Seattle Washington (US)--

Signed and Sealed this  
Twenty-sixth Day of October, 2021

Drew Hirshfeld  
*Performing the Functions and Duties of the*  
*Under Secretary of Commerce for Intellectual Property and*  
*Director of the United States Patent and Trademark Office*